United States Patent [19]

Rothgery et al.

[11] 4,282,169
[45] Aug. 4, 1981

[54] SELECTED 2-ACYL- OR 2-THIOACYL-1-TRI-CHLOROACETIMIDOYLHYDRAZINES AND THEIR USE AS FUNGICIDES

[75] Inventors: Eugene F. Rothgery, North Branford; Lawrence E. Katz, Orande, both of Conn.

[73] Assignee: Olin Corporation, New Haven, Conn.

[21] Appl. No.: 122,202

[22] Filed: Feb. 19, 1980

[51] Int. Cl.³ .............. C07C 109/087; C07C 109/10; A01N 9/20
[52] U.S. Cl. .......................... 260/455 A; 260/465 D; 560/30; 564/74; 564/78; 564/149; 564/150; 564/151; 424/301; 424/311; 424/304; 424/320; 424/324
[58] Field of Search ...................... 260/455 A, 465 D; 560/30; 564/74, 78, 149, 150, 151

[56] References Cited

U.S. PATENT DOCUMENTS

| | | | |
|---|---|---|---|
| 3,541,145 | 11/1970 | van Daalen et al. | 564/74 X |
| 3,668,076 | 6/1972 | Rey et al. | 564/74 X |
| 4,071,633 | 1/1978 | Aoki et al. | 564/149 X |
| 4,166,129 | 8/1979 | Aoki et al. | 564/149 X |

Primary Examiner—Thomas A. Waltz
Attorney, Agent, or Firm—William A. Simons; Thomas P. O'Day

[57] ABSTRACT

Disclosed are selected 2-acyl- or 2-thioacyl-1-trichloroacetimidoylhydrazines having the formula:

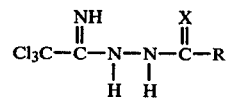

wherein X is an atom selected from the group consisting of oxygen and sulfur; and R is a hydrogen, lower alkyl or lower alkoxy group having 1 to 4 carbon atoms, or an unsubstituted or substituted phenyl group. These compounds are disclosed to be agricultural fungicides.

14 Claims, No Drawings

SELECTED 2-ACYL- OR 2-THIOACYL-1-TRICHLOROACETIMIDOYLHYDRAZINES AND THEIR USE AS FUNGICIDES

BACKGROUND OF THE INVENTION

1. Field of the Invention

This invention relates to selected 2-acyl- or 2-thioacyl-1-trichloroacetimidoylhydrazines and their use as fungicides.

2. Description of the Prior Art

Various acylhydrazines (i.e., compounds with the structure R'—NH—NH—CO—R) are known to possess different types of agricultural pesticidal activity. For example, Chemical Abstracts, 91, 20094r (1979) discloses the use of selected 1-trichloroacetyl-2-benzoylhydrazines as plant disease control agents. Chemical Abstracts, 60, 1606a (1964) discloses the use of chlorinated acetic acid hydrazines as having anti-bacterial activity.

BRIEF SUMMARY OF THE INVENTION

Accordingly, the present invention is directed to, as compositions of matter, selected 2-acyl- or 2-thioacyl-1-trichloroacetimidoylhydrazines of the formula:

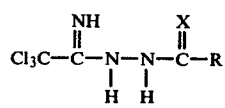

wherein X is an atom selected from the group consisting of oxygen and sulfur; R is a hydrogen or a lower alkyl group having 1 to 4 carbons atoms, or a lower alkoxy group having 1 to 4 carbon atoms, or an unsubstituted or substituted phenyl group. The present invention is also directed to the use of these compounds as fungicides.

DETAILED DESCRIPTION

The acyl- and thioacylhydrazine compounds of the present invention (sometimes generically referred to as "amidrazones") may be prepared by reacting either methyl 2,2,2-trichloroacetimidate or trichloroacetonitrile with the desired hydrazides. These general reactions are illustrated below in equations (A) and (B). In equation (A), methyl 2,2,2-trichloroacetimidate is reacted with acetylhydrazine to form 1-trichloroacetimidoyl-2-acetylhydrazine. In equation (B), trichloroacetonitrile was reacted with ethylxanthylhydrazine to form 1-trichloroacetimidoyl-2-ethylxanthylhydrazine.

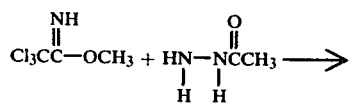

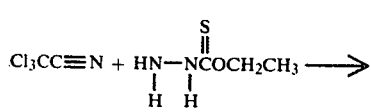

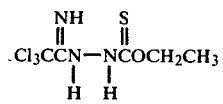

The trichloroacetonitrile reactant is a commercially available chemical. Methyl 2,2,2-trichloroacetimidate may be made by reacting trichloroacetonitrile with methanol in the presence of a base like potassium carbonate. See Chem. Berichte, 91, page 1049 (1958).

The hydrazide reactants may be made by reacting the corresponding acylhalide or thioacylhalides with hydrazine. Alternatively, these hydrazide reactants may be prepared by reacting the corresponding ester with hydrazine. See Hickenbottom, W. J., Reactions of Organic Compounds (3rd Edition), pages 300–301 (1957). Also, lower alkyl and benzylxanthylhydrazines may be made via the reaction of the corresponding alkali metal lower alkyl or benzylxanthates and hydrazine. See K. Ruefenacht, Helvetia Chemica Acta, 51, 518 (1968).

Illustrative carboxylic acid reactants for the compounds of the present invention include the following:
formic hydrazide
acetic hydrazide
propionic hydrazide
butanoic hydrazide
benzoic hydrazide
o-hydroxybenzoic hydrazide (salicylhydrazide)
p-hydroxybenzoic hydrazide
o-,m-,p-methoxybenzoic hydrazide (o-,m-,p-anisic hydrazide)
o-,m-,p-bromobenzoic hydrazide
o-,m-,p-chlorobenzoic hydrazide
o-,m-,p-nitrobenzoic hydrazide
o-,m-,p-toluic hydrazide
ethoxy carbonyl hydrazide (ethyl carbazate)
t-butyl carbonyl hydrazide (t-butyl carbazate)
methyl carbonyl hydrazide (methyl carbazate)

Illustrative thiocarboxylic acid reactants for the compounds of the present invention include the following:
methyl xanthic hydrazide
ethyl xanthic hydrazide
propyl xanthic hydrazide
butyl xanthic hydrazide
benzyl xanthic hydrazide
thioacetic hydrazide
thiobenzoic hydrazide A wide variety of conventional reaction conditions may be employed in the synthesis of the present compounds and the present invention is not intended to be limited to any particular reaction conditions. Advantageously and preferably, the above-noted reactions (A) and (B) are carried out with a molar excess of trichloroacetonitrile or methyl 2,2,2-trichloroacetimidate over the hydrazide reactant. More preferably, from about 0.01 to about 5 moles excess may be employed. The synthesis reactions of the present invention may be carried out in the presence of a suitable organic solvent such as xylene; but a solvent is not necessary, particularly when a relative large molar excess of trichloroacetonitrile or methyl 2,2,2-trichloroacetimidate is used.

Furthermore, the reaction temperature and time will both depend upon many factors including the exact reactants being employed. In most situations, reaction temperatures from about 0° C. to about 100° C., more preferably from about 10° to about 30° C., and reaction times from about 1 hour to about 1 week, more preferably from about 2 hours to about 16 hours, may be employed.

The desired product may be recovered from the reaction mixture by any conventional means, for example, extraction, recrystallization, or the like. Finally, it should be noted that while the reactions illustrated by Equations (A) and (B) are preferred methods for preparing compounds of the present invention, other synthesis methods may also be employed.

Referring to preceding Formula (I), the preferred X is oxygen. When R is a lower alkyl group, methyl is one illustrative substituent. When R is a lower alkoxy group, t-butoxy is one illustrative substituent. When R is a substituted phenyl group, one illustrative phenyl substituent is an ortho-hydroxy group. Other suitable phenyl substituents include lower alkyl groups having 1 to 4 carbon atoms, lower alkoxy groups having 1 to 4 carbon atoms, halo groups such as fluoro, chloro, bromo, iodo, nitro, cyano, meta-hydroxy and para-hydroxy groups.

Representative compounds of the present invention include the following:
1-trichloroacetimidoyl-2-benzoylhydrazine
1-trichloroacetimidoyl-2-acetylhydrazine
1-trichloroacetimidoyl-2-salicoylhydrazine
1-trichloroacetimidoyl-2-(t-butoxycarbonyl)hydrazine
1-trichloroacetimidoyl-2-ethylxanthylhydrazine
1-trichloroacetimidoyl-2-formylhydrazine Also, in accordance with the present invention, it has been found that the compounds of Formula (I) above, may be utilized as effective foliar or soil fungicides. In practicing the process of the present invention, fungi are contacted with a fungicidally effective amount of one or more of these compounds. It is to be understood that the term "fungicidally effective amount" as used in the specification and claims herein is intended to include any amount that will kill or control said foliar or soil fungi when either employed by itself (i.e., in full concentration) or in sufficient concentrations within a carrier or other substance. Of course, this amount may be constantly changing because of the possible variations in many parameters. Some of these may include: the number and type of fungi to be controlled or killed; the type of media to which the present compound can be applied (e.g., plants or soil); degree of effectiveness required; and type of carrier, if any. Generally speaking, applications of an aqueous spray containing at least about 20, more preferably in the range of about 30 to 300, parts per million of the chemical of the present invention may give satisfactory fungi control for most crops.

This step of contacting may be accomplished by applying this compound to the fungi themselves, their habitat, dietary media such as vegetation, crops and the like, including many which these pests may attack.

The above-mentioned compounds of the present invention may be formulated and applied by any conventional methods that include using the compound alone or with a carrier or other substances which may enhance the effectiveness of the chemical or facilitate handling. Moreover, the activity of the present compound may be broadened by the addition thereto of other known pesticides such as other fungicides, herbicides, insecticides and the like.

Specific methods of formulating and applying these active compounds include applying them in the form of dusts, dust or emulsion concentrates, wettable powders and concentrates, granulates, dispersions, sprays, solutions and the like.

The dusts are usually prepared by simply grinding together from about 1% to about 15% by weight of the active compound with a finely divided inert diluent such as walnut flour, diatomaceous earth, fullers earth, attaclay, talc or kaolin. Dust concentrates are made in similar fashion excepting that about 16% to about 75% by weight of active compound is ground usually together with the diluent. In practice, dust concentrates are then generally admixed at the site of use with more inert diluent before it is applied to the plant foliage, soil, or animals which are to be protected from fungi attack.

Wettable powders are generally prepared in the same manner as dust concentrates, but usually about 1% to about 10% by weight of a dispersing agent, for example, an alkali metal lignosulfonate and about 1% to about 10% of a surfactant, such as a non-ionic surfactant, are incorporated in the formulation. For application to agronomic crops, shrubs, ornamentals and the like, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray or dip application.

It is possible to formulate granulates whereby the active compound is dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, the above-mentioned active compound is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that the fungicide formulations, the ingredients which may make up such formulations other than the active compound, the dosages of these ingredients, and means of applying these formulations may include all known and conventional substances, amounts and means, respectively, that are suitable for obtaining the desired fungicidal result. And, therefore, such process parameters are not critical to the present invention.

Fungicides of the present invention may be effective for the control of broad classes of foliar and soil fungi. Specific illustrations of foliar fungi wherein fungicidal activity has been shown include bean rust and cucumber anthracnose. A specific illustration of soil fungus wherein fungicidal activity has been shown is black root rot.

The following examples further illustrate the present invention. All parts and percentages employed therein are by weight unless otherwise indicated. Yields given are percent molar yields.

EXAMPLE 1

Preparation of 1-Trichloroacetimidoyl-2-Benzoylhydrazine

A mixture of 9.1 g (0.07 mole) benzoylhydrazine and 20 ml (28.5 g, 0.16 mole) methyl 2,2,2-trichloroacetimidate was stirred 16 hours at room temperature. The solid that was left was washed with petroleum ether and dried to give 18.6 g (100% yield) of product (mp 170°–172° C.). A sample recrystallized from ethanol had mp 178°–181° C. The structure was confirmed via infrared and elemental analysis.

Analysis for $C_9H_8N_3Cl_3O$

|  | C | H | N | Cl |
|---|---|---|---|---|
| Calculated | 38.53 | 2.87 | 14.98 | 37.92 |
| Found | 38.37 | 2.95 | 15.13 | 37.76 |

EXAMPLE 2

Preparation of 1-Trichloroacetimidoyl-2-Acetylhydrazine

A mixture of 5.0 g (0.07 mole) acetylhydrazine and 20 ml (28.5 g, 0.16 mole) methyl 2,2,2-trichloroacetimidate was stirred 16 hours at room temperature. The resulting solid was recrystallized from toluene to yield 7.3 g. Addition of petroleum ether to the filtrate gave another 1.5 g. The total yield was 8.8 g (59%; mp 130°–132° C.). An analytical sample (mp 131°–132° C.) was prepared by recrystallization from toluene. The structure was confirmed via infrared and elemental analysis.

Analysis for $C_4H_6N_3Cl_3O$

|  | C | H | N | Cl |
|---|---|---|---|---|
| Calculated | 21.99 | 2.77 | 19.23 | 48.69 |
| Found | 22.20 | 2.71 | 19.35 | 48.36 |

EXAMPLE 3

Preparation of 1-Trichloroacetimidoyl-2-Salicoylhydrazine

A mixture of 3.8 g (0.025 mole) salicoylhydrazine and 10 ml (14.3 g, 0.08 mole) methyl 2,2,2-trichloroacetimidate was stirred 16 hours at room temperature. The solid that formed was washed with petroleum ether and dried to give 7.5 g (100% Yield; mp 168°–169° C.). The structure was confirmed via infrared and elemental analysis.

Analysis for $C_9H_8N_3Cl_3O_2$

|  | C | H | N | Cl |
|---|---|---|---|---|
| Calculated | 36.46 | 2.72 | 14.17 | 35.88 |
| Found | 36.22 | 2.67 | 14.14 | 36.06 |

EXAMPLE 4

Preparation of 1-Trichloroacetimidoyl-2-(t-Butoxycarbonyl)hydrazine

A mixture of 2.9 g (0.025 mole) t-butyl carbazate and 10 ml (14.3 g, 0.08 mole) methyl 2,2,2-trichloroacetimidate was stirred 16 hours at room temperature. The solid that was left was washed with petroleum ether and dried to give 6.0 g (86% yield mp 150° C.). The structure was confirmed via infrared and elemental analysis.

Analysis for $C_7H_{12}N_3Cl_3O_2$

|  | C | H | N | Cl |
|---|---|---|---|---|
| Calculated | 30.40 | 4.38 | 15.19 | 38.46 |
| Found | 30.20 | 4.20 | 15.14 | 38.62 |

EXAMPLE 5

Preparation of 1-Trichloroacetimidoyl-2-Ethylxanthylhydrazine

A mixture of 14.4 g (0.1 mole) trichloroacetonitrile and 12.0 g (0.1 mole) of ethylxanthylhydrazine was stirred at 10° C. for 2 hours. The reaction mixture was allowed to attain room temperature while being stirred. The reaction exothermed to 45° C. and was then cooled to room temperature. The solid that formed was filtered, washed with cooled ether, and dried to give 8.1 g (mp 117°–118° C.). A second crop of 4.1 g was obtained from the filtrate. The total yield was 12.2 g (46%). The structure was confirmed via infrared and elemental analysis.

Analysis for $C_5H_8N_3Cl_3SO$

|  | C | H | N | Cl | S |
|---|---|---|---|---|---|
| Calculated | 22.71 | 3.05 | 15.89 | 40.21 | 12.11 |
| Found | 22.50 | 3.09 | 16.06 | 40.29 | 12.12 |

EXAMPLE 6

Preparation of 1-Trichloroacetimidoyl-2-Formylhydrazine

A mixture of 4.2 g (0.07 mole) formylhydrazine and 20 ml (28.5 g, 0.16 mole) methyl 2,2,2-trichloroacetimidate was stirred at room temperature. After 10 minutes a vigorous reaction occurred and the temperature rose to 65° C. The beige solid that formed was washed with petroleum ether and dried to give 11.0 g [77%, mp 124°–126° C. (decomposed)] of product. An analytical sample was recrystallized from toluene [mp 128°–130° C. (decomposed)]. The structure was confirmed via infrared and elemental analysis.

Analysis for $C_3H_4N_4Cl_3O$

|  | C | H | N | Cl |
|---|---|---|---|---|
| Calculated | 17.62 | 1.97 | 20.55 | 52.03 |
| Found | 17.64 | 1.87 | 20.74 | 51.78 |

FOLIAR FUNGICIDE SCREEN

The active materials formed in Examples 1–6 were then tested for activity as effective fungicides.

A uniform aqueous dispersion of each chemical made in the above examples was first prepared. These dispersions were made by dissolving each chemical in a solution of acetone containing the surfactant TRITON X-155[1] (concentration 500 parts per million). Next, this solution was diluted with water 1:9 to obtain a stock solution of 10% by volume acetone and 90% by volume water with 50 ppm TRITON X-155 and the test chemical contained therein. This stock solution was diluted further with water/acetone mix to provide the desired concentration of the test material, if required.

[1]Manufactured by *Rohm and Haas* of Philadelphia, PA and is a polyether alcohol.

The aqueous solutions containing each chemical were applied to various plants according to the methods stated below. These tests were designed to evaluate the ability of the chemical to protect non-infected foliage and eradicate recently established infection against majot types of fungi such as rust and anthracnose that attack above-ground parts of plants.

BEAN RUST

Pinto beans, which were in 2½ inch pots and 9 to 12 days old, were sprayed and the soil drenched with an aqueous solution of the chemical of the present invention. The young plants were sprayed while rotating the plants on a turntable and the aqueous solution contained 260 parts per million of the chemical. After the spray deposit had dried, the plants were atomized with a suspension of uredospores [summer spore stage of bean rust (*Uromyces phaseoli*)] and placed in a moist chamber at 70° F. for 24 hours. After 7 days, the severity of pustule formation was rated on a scale of 0 (no inhibition) to 10 (complete inhibition). See Table I for the results of these tests.

CUCUMBER ANTHRACNOSE

Two week old cucumber plants were atomized with a suspension of cucumber anthracnose spores (*Collectotrichium lagenarium*) and placed in a moist chamber at 70° F. for 24 hours. The young plants were then sprayed while rotating the plants on a turntable with an aqueous solution that contained 260 parts per million of the chemical of the present invention. After 5 days, the severity of pustule formation was rated on a scale of 0 (no inhibition) to 10 (complete inhibition). See Table I for the results of these tests.

SOIL FUNGICIDE TEST

Thielaviopsis basicola was cultured on a sterile medium of corn meal and No. 4 zonolite in several petri dishes. The culture was then blended with sterile soil in individual containers. Ten mung bean seeds were pressed into the infested soil in each container and covered with additional infested soil. The stock solution containing active compounds of Examples 1-6 were then added in the amount of 50 lb/acre and each container was held closed for three days and then opened for eleven additional days. Each test was then scored on the basis of plant emergence and control of disease (black root rot) in each plant. Thus, a 10 represented the highest possible score and 0 represented the lowest. The test results are given in Table I.

TABLE 1

| | Fungicidal Activity | | |
| | Foliar Fungi | | |
| Example | Bean Rust | Cucumber Anthracnose | Soil Fungus *Thielaviopsis basicola* |
|---|---|---|---|
| 1 | 10; 9[a] | 10 | 0 |
| 2 | 4 | 9 | 3 |
| 3 | 4 | 10 | 8 |
| 4 | 6 | 8 | 0 |
| 5 | 10 | 0 | 3 |
| 6 | 4 | 0 | 0 |

[a]Further foliage testing at 33 ppm gave a score of 9

What is claimed is:

1. A compound of the formula:

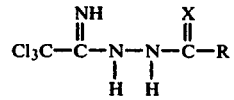

wherein X is an atom selected from the group consisting of oxygen and sulfur; and R is hydrogen, a lower alkyl group having 1 to 4 carbon atoms, a lower alkoxy group having 1 to 4 carbon atoms, or an unsubstituted or substituted phenyl group.

2. The compound of claim 1 wherein the substituents of said substituted phenyl group are selected from the group consisting of lower alkyl groups having 1 to 4 carbons atoms, lower alkoxy groups having 1 to 4 carbons atoms, halo, nitro, cyano and hydroxy.

3. The compound of claim 1 wherein X is oxygen.

4. The compound of claim 3 wherein R is a lower alkyl group.

5. The compound of claim 3 wherein R is a phenyl group.

6. The compound of claim 3 wherein R is a lower alkoxy group.

7. The compound of claim 3 wherein R is a substituted phenyl group.

8. The compound of claim 3 wherein R is hydrogen.

9. The compound of claim 1 wherein X is sulfur.

10. The compound of claim 9 wherein R is a lower alkyl group.

11. The compound of claim 9 wherein R is a lower alkoxy group.

12. The compound of claim 9 wherein R is a phenyl group.

13. The compound of claim 9 wherein R is a substituted phenyl group.

14. The compound of claim 9 wherein R is hydrogen.

* * * * *